(12) United States Patent
Li et al.

(10) Patent No.: US 12,410,175 B2
(45) Date of Patent: Sep. 9, 2025

(54) COMPOUNDS

(71) Applicant: INTRA-CELLULAR THERAPIES, INC., New York, NY (US)

(72) Inventors: Peng Li, New Milford, NJ (US); Robert Davis, San Diego, CA (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 758 days.

(21) Appl. No.: 17/753,472

(22) PCT Filed: Sep. 3, 2020

(86) PCT No.: PCT/US2020/049141
§ 371 (c)(1),
(2) Date: Mar. 3, 2022

(87) PCT Pub. No.: WO2021/046179
PCT Pub. Date: Mar. 11, 2021

(65) Prior Publication Data
US 2022/0356187 A1    Nov. 10, 2022

Related U.S. Application Data

(60) Provisional application No. 62/895,477, filed on Sep. 3, 2019.

(51) Int. Cl.
*C07D 487/14* (2006.01)
*A61K 38/00* (2006.01)

(52) U.S. Cl.
CPC .......... *C07D 487/14* (2013.01); *A61K 38/005* (2013.01)

(58) Field of Classification Search
CPC .................................................. C07D 487/14
USPC ........................................................ 514/267
See application file for complete search history.

(56) References Cited

U.S. PATENT DOCUMENTS

| | | | |
|---|---|---|---|
| 5,202,328 A | 4/1993 | de Laszlo et al. | |
| 5,294,612 A | 3/1994 | Bacon et al. | |
| 5,393,755 A | 2/1995 | Neustadt et al. | |
| 5,824,683 A | 10/1998 | McKittrick et al. | |
| 5,849,770 A | 12/1998 | Head et al. | |
| 5,939,419 A | 8/1999 | Tulshian et al. | |
| 5,962,492 A | 10/1999 | Warrellow et al. | |
| 6,013,621 A | 1/2000 | Nishi et al. | |
| 6,133,273 A | 10/2000 | Gilbert et al. | |
| 6,221,335 B1* | 4/2001 | Foster .................. | C07B 59/002 424/1.81 |
| 6,235,742 B1 | 5/2001 | Bell et al. | |
| 6,235,746 B1 | 5/2001 | Davis et al. | |
| 6,316,444 B1 | 11/2001 | Hunt et al. | |
| 6,423,716 B1 | 7/2002 | Matsuno et al. | |
| 6,440,710 B1 | 8/2002 | Keinan et al. | |
| 6,492,371 B2 | 12/2002 | Roylance | |
| 6,498,165 B1 | 12/2002 | Armstrong et al. | |
| 6,552,029 B1 | 4/2003 | Davis et al. | |
| 6,586,423 B2 | 7/2003 | Bilodeau et al. | |
| 6,599,908 B1 | 7/2003 | Davis et al. | |
| 6,603,008 B1* | 8/2003 | Ando ....................... | A61P 7/04 546/271.4 |
| 6,649,608 B2 | 11/2003 | Pease et al. | |
| 6,670,368 B1 | 12/2003 | Breault et al. | |
| 6,693,099 B2 | 2/2004 | Degenhardt et al. | |
| 6,756,373 B1 | 6/2004 | Allerton et al. | |
| 6,969,719 B2 | 11/2005 | Asberom et al. | |
| 7,153,824 B2 | 12/2006 | Palmer et al. | |
| 7,157,451 B2 | 1/2007 | Atwal et al. | |
| 7,517,990 B2* | 4/2009 | Ito ....................... | C07D 233/56 546/184 |
| 8,273,750 B2 | 9/2012 | Li et al. | |
| 8,273,751 B2 | 9/2012 | Li et al. | |
| 8,536,159 B2 | 9/2013 | Li et al. | |
| 8,633,180 B2 | 1/2014 | Li et al. | |
| 8,664,207 B2 | 3/2014 | Li et al. | |
| 8,697,710 B2 | 4/2014 | Li et al. | |
| 9,884,872 B2 | 2/2018 | Li | |
| 10,131,671 B2 | 11/2018 | Li et al. | |
| 10,150,774 B2 | 12/2018 | Li et al. | |
| 2003/0069246 A1 | 4/2003 | Darrow et al. | |
| 2003/0092908 A1 | 5/2003 | Pitts et al. | |
| 2003/0162782 A1 | 8/2003 | Grossman et al. | |
| 2004/0087517 A1 | 5/2004 | Burnet et al. | |

(Continued)

FOREIGN PATENT DOCUMENTS

| | | |
|---|---|---|
| DE | 199 31 206 A1 | 1/2001 |
| EP | 0 063 381 A1 | 10/1982 |

(Continued)

OTHER PUBLICATIONS

Morrison and Boyd, 3rd ed. (1973), pp. 353-354.*
Tonn et al., Biol. Mass Spec. (1993) 22:633-42.*
Timmins, Expert Opin. Ther. Patents (2014) 24(10), pp. 1067-1075.*
Li et al., "Discovery of Potent and Selective Inhibitors of Phosphodiesterase 1 for the Treatment of Cognitive Impairment Associated with Neurodegenerative and Neuropsychiatric Diseases," *J. Med. Chem.*, vol. 59, pp. 1149-1164 (2016).
Mani et al., "Requirement for DARPP-32 in Progesterone-Facilitated Sexual Receptivity in Female Rats and Mice," *Science*, vol. 287, pp. 1053-1056, (2000).
Timmins et al., "Deuterated Drugs: Where are we now?," *Expert Opin Ther Pat.*, vol. 24, No. 10, pp. 1067-1075, (2014).
"Anxiety," [retrieved on May 14, 2008]. Retrieved online via Internet, URL: http://www.nlm.nih.gov/medlineplus/anxiety.html, 5 pages.

(Continued)

*Primary Examiner* — Taofiq A Solola
(74) *Attorney, Agent, or Firm* — Hoxie & Associates LLC

(57) ABSTRACT

The present invention relates to PDE1 inhibitory compounds useful in the treatment of diseases involving disorders of the dopamine D1 receptor intracellular pathway, such as, among others, Parkinson's disease, depression, narcolepsy, psychosis, damage to cognitive function, e.g., in schizophrenia, or disorders that may be ameliorated through enhanced progesterone-signaling pathway, as well as their use as pharmaceuticals and pharmaceutical compositions comprising them. Methods of making and methods of use related to such compounds are further described.

7 Claims, No Drawings

(56) References Cited

U.S. PATENT DOCUMENTS

| | | |
|---|---|---|
| 2004/0259792 A1 | 12/2004 | Palmer et al. |
| 2005/0075795 A1 | 4/2005 | Pandit |
| 2005/0113379 A1 | 5/2005 | Ge et al. |
| 2005/0176814 A1 | 8/2005 | Alken |
| 2006/0252790 A1 | 11/2006 | Allen et al. |
| 2007/0082929 A1* | 4/2007 | Gant .............. A61P 43/00 546/273.7 |
| 2007/0197695 A1* | 8/2007 | Potyen .............. C08K 5/55 524/110 |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2010/0087450 A1 | 4/2010 | Mates et al. |
| 2010/0173878 A1 | 7/2010 | Li et al. |
| 2010/0273753 A1 | 10/2010 | Li et al. |
| 2010/0273754 A1 | 10/2010 | Li |
| 2010/0323997 A1 | 12/2010 | Fienberg et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1 | 3/2012 | Fienberg et al. |
| 2012/0071450 A1 | 3/2012 | Li et al. |
| 2012/0094966 A1 | 4/2012 | Li et al. |
| 2012/0136013 A1 | 5/2012 | Li et al. |
| 2012/0201754 A1 | 8/2012 | Li |
| 2012/0238589 A1 | 9/2012 | Li et al. |
| 2013/0018063 A1 | 1/2013 | Li et al. |
| 2013/0085123 A1 | 4/2013 | Li et al. |
| 2013/0239234 A1 | 9/2013 | Greengard et al. |
| 2013/0324565 A1 | 12/2013 | Li et al. |
| 2013/0331363 A1 | 12/2013 | Li et al. |
| 2013/0338124 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1 | 7/2014 | Li et al. |
| 2014/0315868 A1 | 10/2014 | Li et al. |
| 2021/0379072 A1 | 12/2021 | Davis et al. |

FOREIGN PATENT DOCUMENTS

| | | |
|---|---|---|
| EP | 0 095 289 A2 | 11/1983 |
| EP | 0 201 188 A2 | 12/1986 |
| EP | 0 636 626 A1 | 2/1995 |
| EP | 0 911 333 A1 | 4/1999 |
| JP | 53031694 A | 3/1978 |
| KR | 10-1991-0006866 | 9/1991 |
| WO | WO-91/19719 A1 | 12/1991 |
| WO | WO-94/19351 A1 | 9/1994 |
| WO | WO-95/26325 A2 | 10/1995 |
| WO | WO-98/46606 A1 | 10/1998 |
| WO | WO-98/52568 A1 | 11/1998 |
| WO | WO-01/27113 A1 | 4/2001 |
| WO | WO-02/074312 A1 | 9/2002 |
| WO | WO-03/002567 A1 | 1/2003 |
| WO | WO-03/020702 A2 | 3/2003 |
| WO | WO-03/020724 A1 | 3/2003 |
| WO | WO-03/042216 A1 | 5/2003 |
| WO | WO-2006/133261 A2 | 12/2006 |
| WO | WO-2007/143568 A1 | 12/2007 |
| WO | WO-2007/143705 A2 | 12/2007 |
| WO | WO-2008/063505 A1 | 5/2008 |
| WO | WO-2009/073210 A1 | 6/2009 |
| WO | WO-2009/075784 A1 | 6/2009 |
| WO | WO 2010/065151 A1 | 6/2010 |
| WO | WO 2010/132127 A1 | 11/2010 |
| WO | WO-2011/043816 A1 | 4/2011 |
| WO | WO-2011/153129 A1 | 12/2011 |
| WO | WO-2011/153135 A1 | 12/2011 |
| WO | WO-2011/153136 A1 | 12/2011 |
| WO | WO-2011/153138 A1 | 12/2011 |
| WO | WO-2012/171016 A1 | 12/2012 |
| WO | WO-2013/192556 A2 | 12/2013 |
| WO | WO-2014/145617 A2 | 9/2014 |
| WO | WO-2014/151409 A1 | 9/2014 |
| WO | WO-2014/205354 A2 | 12/2014 |
| WO | WO-2015/106032 A1 | 7/2015 |
| WO | 2015/196186 * | 12/2015 |

OTHER PUBLICATIONS

"Autism," [retrieved on May 14, 2008]. Retrieved online via Internet, URL: http://www.nlm.nih.gov/medlineplus/autism.html, 6 pages.

Abstract for EP 0 063 381 A1 (WO8203626A1).

Ahn et al., "Potent Tetracyclic Guanine Inhibitors of PDE1 and PDE5 Cyclic Guanosine Monophosphate Phosphodiesterases with Oral Antihypertensive Activity," Journal of Medicinal Chemistry, vol. 40, No. 14, p. 2196-2210, (1997).

Al-Afaleq et al., "Heterocyclic o-Aminonitriles: Preparation of Pyrazolo[3,4-d]-pyrimidines with Modification of the Substituents at the 1-Position," Molecules, vol. 6, p. 621-638, (2001).

Aswar et al., "Anti-Cataleptic Activity of Various Extracts of Ocimum Sanctum," International Journal of Pharmaceutical Research and Development, vol. 2, No. 6, 7 pages, (2010).

Baillie, T.A., "The Use of Stable Isotopes in Pharmacological Research," Pharmacological Reviews, vol. 33, No. 2, p. 81-132, (1981).

Banker, Gilbert S. et al., Eds., Modern Pharmaceutics, Third Edition, Marcel Dekker Inc., New York, 1996.

Bastia et al., "Effect of A1 and A2A Adenosine Receptor Ligands in Mouse Acute Models of Pain," Neuroscience Letters, vol. 328, p. 241-244, (2002).

Bender et al., "Cyclic Nucleotide Phosphodiesterases: Molecular Regulation to Clinical Use," Pharmacological Reviews, vol. 58, No. 3, p. 488-520, (2006).

Blake et al., "Studies with Deuterated Drugs," Review Article, Journal of Pharmaceutical Sciences, vol. 64, No. 3, 26 pages, (1975).

Blokland et al., "PDE Inhibition and Cognition Enhancement," vol. 22, No. 4, p. 349-354, (2012); Abstract Only.

Boyd et al., "Dopamine Receptor Signaling and Current and Future Antipsychotic Drugs" in Current Antipsychotics, Handbook of Experimental Pharmacology, vol. 212, Gross, G. et al., Eds., doi:10.1007/978-3-642-25761-2_3, Springer-Verlag, Berlin, pp. 53-86, (2012).

Browne, T.R., "Stable Isotope Techniques in Early Drug Development: An Economic Evaluation," J Clin Pharacol., vol. 38, p. 213-220, (1998).

Burnouf et al., "Synthesis, Structure-Activity Relationships, and Pharmacological Profile of 9-Amino-4-oxo-1-phenyl-3,4,6,7-tetrahydro[1,4]diazepino[6,7,1-hi]indoles: Discovery of Potent, Selective Phosphodiesterase Type 4 Inhibitors," Journal of Medicinal Chemistry, vol. 43, No. 25, p. 4850-4867, (2000).

Buteau, K.C., "Deuterated Drugs: Unexpectedly Nonobvious?," Journal of High Technology Law, vol. X, No. 1, 28 pages, (2009).

Chalimoniuk et al., "Upregulation of Guanylyl Cyclase Expression and Activity in Striatum of MPTP-induced Parkinsonism in Mice," Biochemical and Biophysical Research Communications, vol. 324, p. 118-126, (2004).

Chebib et al., "1-Phenylpyrazolo[3,4-d]pyrimidines; Structure-Activity Relationships for C6 Substituents at A1 and A2A Adenosine Receptors," Bioorganic & Medicinal Chemistry, vol. 8, p. 2581-2590, (2000).

Chen et al., "Effects of Bimatoprost 0.03% on Ocular Hemodynamics in Normal Tension Glaucoma," Journal of Ocular Pharmacology and Therapeutics, vol. 22, No. 3, p. 188-193, (2006).

Chermat et al., "Adaptation of the Tail Suspension Test to the Rat," Journal de Pharmacologie (Paris), vol. 17. No. 3, p. 348-350, (1986).

Cherrah et al., "Study of Deuterium Isotope Effects on Protein Binding by Gas Chromatography/Mass Spectrometry. Caffeine and Deuterated Isotopomers," Biomedical and Environmental Mass Spectrometry, vol. 14, p. 653-657, (1987).

(56) References Cited

OTHER PUBLICATIONS

Deshmukh et al., "Amelioration of Intracerebroventricular Streptozotocin Induced Cognitive Dysfunction and Oxidative Stress by Vinpocetine—A PDE1 Inhibitor," European Journal of Pharmacology, vol. 620, No. 1-3, p. 49-56, (2009).
Dewald et al., "Synthesis and Potential Antipsychotic Activity of 1H-Imidazo[1,2-c]pyrazolo[3,4-e]pyrimidines," Journal of Medicinal Chemistry, vol. 31, p. 454-461, (1988).
Dyck et al., "Effects of Deuterium Substitution on the Catabolism of Beta-Phenylethylamine: An In Vivo Study," Journal of Neurochemistry, vol. 46, No. 2, 6 pages, (1986).
Ehrman et al., "Phosphodiesterase 1B Differentially Modulates the Effects of Methamphetamine on Locomotor Activity and Spatial Learning Through DARPP32-Dependent Pathways: Evidence from PDE1B-DARPP32 Double-Knockout Mice," Genes, Brain and Behavior, vol. 5, No. 7, p. 540-551, (2006).
Ennaceur et al., "A New One-Trial Test for Neurobiological Studies of Memory in Rats. 1:Behavioral Data," Behavioural Brain Research, vol. 31, p. 47-59, (1998).
Fienberg et al., "DARPP-32: Regulator of the Efficacy of Dopaminergic Neurotransmission," Science, vol. 281, p. 838-842, (1998).
Filgueiras et al., "Phosphodiesterase Type 1 Inhibition Improves Learning in Rats Exposed to Alcohol During the Third Trimester Equivalent of Human Gestation," Neuroscience Letters, vol. 473, No. 3, p. 202-207, (2010).
Foster, A.B., "Deuterium Isotope Effects in the Metabolism of Drugs and Xenobiotics: Implications for Drug Design," Advances in Drug Research, vol. 14, p. 1-40, (1985).
Gelbin et al., "Ketene-S,N-acetals as Synthons for Heterocycles, New Synthesis of Pyrimidinones," Journal Für Praktische Chemie, vol. 329, No. 5, p. 753-766, (1987).
Goodman & Gilman, Las bases farmacológicas de la terapéutica (The Pharmacological Basis of Therapeutics), McGraw-Hill Interamericana, 2007, p. 892, cited within text of Opposition to Letters Patent in Costa Rican Patent Application No. 2011-0313, 7 pages.
Gouyette, A., "Synthesis of Deuterium-labelled Elliptinium and its Use in Metabolic Studies," Biomedical and Environmental Mass Spectrometry, vol. 15, p. 243-247, (1988).
Greengard et al., "Beyond the Dopamine Receptor: The DARPP-32/Protein Phosphatase-1 Cascade," Neuron, vol. 23, p. 435-447, (1999).
Han et al., "The Calcium/Calmodulin-dependent Phosphodiesterase PDE1C Down-regulates Glucose-induced Insulin Secretion," The Journal of Biological Chemistry, vol. 274, No. 32, p. 22337-22344, (1999).
Haskins, N.J., "The Application of Stable Isotopes in Biomedical Research," Review Paper, Biomedical Mass Spectrometry, vol. 9, No. 7, p. 269-277, (1982).
Honma et al., "The Metabolism of Roxatidine Acetate Hydrochloride: Liberation of Deuterium from the Piperidine Ring During Hydroxylation," Drug Metabolism and Disposition, vol. 15, No. 4, p. 551-559, (1987).
Hulley et al., "Cyclic AMP Promotes the Survival of Dopaminergic Neurons in vitro and Protects Them from the Toxic Effects of MPP+," Journal of Neural Transmission [Supplemental], vol. 46, p. 217-228, (1995).
International Search Report of International Application No. PCT/US2015/036890, prepared by the International Searching Authority, date mailed: Sep. 14, 2015, 4 pages.
Japanese Patent Office, Patent Abstracts of Japan, Abstract for JP 53031694 A, Date of publication of application Mar. 25, 1978, 1 page.
Jiang et al., "Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol," Journal of Organic Chemistry, vol. 70, p. 2824-2827, (2005).
Kakkar et al. "Amantadine: An Antiparkinsonian Agent Inhibits Bovine Brain 60 kDa Calmodulin-Dependent Cyclic Nucleotide Phosphodiesterase Isozyme," Brain Research, vol. 749, No. 2, p. 290-294, (1997).
Kakkar et al. "Calmodulin-dependent Cyclic Nucleotide Phosphodiesterase (PDE1)," CMLS Cellular and Molecular Life Sciences, vol. 55, No. 8-9, p. 1164-1186, (1999).
Kakkar et al., "Inhibition of Bovine Brain Calmodulin-Dependent Cyclic Nucleotide Phosphodiesterase Isozymes by Deprenyl," Life Sciences, vol. 59, No. 21, p. 337-341, (1996).
Klaissle et al., "Physical Activity and Environmental Enrichment Regulate the Generation of Neural Precursors in the Adult Mouse Substantia Nigra in a Dopamine-dependent Manner," BMC Neuroscience, vol. 13, No. 132, doi:10.1186/1471-2202-13-132, 15 pages, (2012).
Kleppisch, T., "Phosphodiesterases in the Central Nervous System" in cGMP: Generators, Effectors and Therapuetic Implications, Handbook of Experimental Pharmacology, vol. 191, Schmidt, H. et al., Eds., Springer-Verlag, Berlin, p. 71-92, (2009).
Laddha et al., "A New Therapeutic Approach in Parkinson's Disease: Some Novel Quinazoline Derivatives as Dual Selective Phosphodiesterase 1 Inhibitors and Anti-inflammatory Agents" Bioorganic & Medicinal Chemistry, vol. 17, No. 19, p. 6796-6802, (2009).
Lundqvist et al., "Exploitation of Structural and Regulatory Diversity in Glutamate Racemases," Nature, vol. 447, p. 817-822, (2007).
Medina, A., "Therapeutic Utility of Phosphodiesterase Type 1 Inhibitors in Neurological Conditions," Frontiers in Neuroscience, vol. 5, No. 21, 6 pages, (2011).
Murray et al., "Expression and Activity of CAMP Phosphodiesterase Isoforms in Pulmonary Artery Smooth Muscle Cells from Patients with Pulmonary Hypertension: Role for PDE1," American Journal of Physiology, Lung Cellular and Molecular Physiology, vol. 292, p. L294-L303, (2007).
Murray et al., "LY503430, A Novel -Amino-3-hydroxy-5-methylisoxazole-4-propionic Acid Receptor Potentiator with Functional, Neuroprotective and Neurotrophic Effects in Rodent Models of Parkinson's Disease," The Journal of Pharmacology and Experimental Therapeutics, vol. 306, No. 2, p. 752-762, (2003).
Nishi et al., "Advanced Research on Dopamine Signaling to Develop Drugs for the Treatment of Mental Disorders: Biochemical and Behavioral Profiles of Phosphodiesterase Inhibition in Dopaminergic Neurotransmission," Journal of Pharmacological Sciences, vol. 114, p. 6-16, (2010).
Noguchi et al., "A Facile Preparation of 7-(Substituted Amino-)-6H-pyrrolo[3,4-d]-pyrimidine Derivatives," Bulletin of the Chemical Society of Japan, vol. 62, No. 9, p. 3043-3045, (1989).
Pardo et al., "Synthesis of 1-(p-Nitrobenzyl)Azoles and 1-(p-Nitrobenzyl)Benzazoles," OPPI Briefs, vol. 32, No. 4, p. 385-390, (2000).
Park et al., "Traumatic Brain Injury: Can the Consequences Be Stopped?" CMAJ, vol. 178, No. 9, p. 1163-1170, (2008).
Pieniaszek et al., "Moricizine Bioavailability via Simultaneous, Dual, Stable Isotope Administration: Bioequivalence Implications," J Clin Pharmacol., vol. 39, p. 817-825, (1999).
Polli et al., "Expression of a Calmodulin-dependent Phosphodiesterase Isoform (PDE1B1) Correlates With Brain Regions Having Extensive Dopaminergic Innervation," The Journal of Neuroscience, vol. 14, No. 3, p. 1251-1261, (1994).
Porsolt et al., "Depression: A New Animal Model Sensitive to Antidepressant Treatments," Nature, vol. 266, p. 730-732, (1977).
Poulsen et al., "High-Pressure Synthesis of Enantiomerically Pure C-6 Substituted Pyrazolo[3,4-d]pyrimidines," Biorganic & Medicinal Chemistry Letters, vol. 11, p. 191-193, (2001).
Prickaerts et al., "Possible Role of Nitric Oxide-Cyclic GMP Pathway in Object Recognition Memory: Effects of 7-Nitroindazole and Zaprinast," European Journal of Pharmacology, vol. 337, p. 125-136, (1997).
Reed et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, vol. 22, No. 12, p. 5188-5197, (2002).

(56) References Cited

OTHER PUBLICATIONS

Rybalkin et al., "Cyclic GMP Phosphodiesterases and Regulation of Smooth Muscle Function," Circulation Research, vol. 93, p. 280-291, (2003).
Sanderson, K., "Big Interest in Heavy Drugs," Nature Jobs, vol. 458, p. 269, (2009).
Schmidt, C., "Phosphodiesterase Inhibitors as Potential Cognition Enhancing Agents," Current Topics in Medicinal Chemistry, vol. 10, No. 2, p. 222-230, (2010).
Sharma et al., "Regulation of Calmodulin-Stimulated Cyclic Nucleotide Phosphodiesterase (PDE1): Review," International Journal of Molecular Medicine, vol. 18, p. 95-105, (2006).
Shimizu et al., "Calmodulin-Dependent Cyclic Nucleotide Phosphodiesterase (PDE1) Is a Pharmacological Target of Differentiation-Inducing Factor-1, an Antitumor Agent Isolated from Dictyostelium," Cancer Research, vol. 64, p. 2568-2571, (2004).
Shook et al., "Design and Characterization of Optimized Adenosine A2A/A1 Receptor Antagonists for the Treatment of Parkinson's Disease," Journal of Medicinal Chemistry, doi:10.1021/jm201640m, 47 pages, (2012).
Tonn et al., "Simultaneous Analysis of Diphenhydramine and a Stable Isotope Analog (2H10)diphenhydramine Using Capillary Gas Chromatography with Mass Selective Detection in Biological Fluids from Chronically Instrumented Pregnant Ewes," Biol Mass Spectrom., vol. 22, No. 11, p. 633-642, (1993); Abstract Only.
Turko et al., "Inhibition of Cyclic GMP-Binding Cyclic GMP-Specific Phosphodiesterase (Type 5) by Sildenafil and Related Compounds," Molecular Pharmacology, vol. 56, p. 124-130, (1999).
Ungerstedt et al., "Quantitative Recording of Rotational Behavior in Rats After 6-Hydroxy-dopamine Lesions of the Nigrostriatal Dopamine System," Brain Research, vol. 24, p. 485-493, (1970).
Ungerstedt, U., "Stereotaxic Mapping of the Monoamine Pathways in the Rat Brain," Acta Physiologica Scandinavica, Supplementum 367, p. 1-48, (1971).
Vatter et al., "Differential Phosphodiesterase Expression and Cytosolic Ca2+ in Human CNS Tumour Cells and in Non-Malignant and Malignant Cells of Rat Origin," Journal of Neurochemistry, vol. 93, p. 321-329, (2005).
Wolen, R.L., "The Application of Stable Isotopes to Studies of Drug Bioavailability and Bioequivalence," J Clin Pharmacol., vol. 26, No. 6, p. 419-424, (1986); Abstract Only.
Wolff, M. Ed., Burger's Medicinal Chemistry and Drug Discovery, Fifth Edition, vol. I: Principles and Practice, John Wiley & Sons, New York, p. 975-977, (1995).
Xia et al., "Synthesis and Evaluation of Polycyclic Pyrazolo[3,4-d]pyrimidines as PDE1 and PDE5 cGMP Phosphodiesterase Inhibitors," Journal of Medicinal Chemistry, vol. 40, p. 4372-4377, (1997).
Ahlström, M., et al. "Cyclic Nucleotide Phosphodiesterases (PDEs) in Human Osteoblastic Cells; The Effect of PDE Inhibition on cAMP Accumulation," Cell Mol Biol Lett, vol. 10, No. 2, pp. 305-319, (2005).
Amin, S., et al. "Exploring pyrazolo[3,4-d]pyrimidine phosphodiesterase 1 (PDE1) inhibitors: a predictive approach combining comparative validated multiple molecular modelling techniques," Journal of Biomolecular Structure and Dynamics, vol. 36, No. 3, pp. 590-608, (2018).
Brodbelt et al., "Glioblastoma in England: 2007-2011," Eur J Cancer, vol. 51, pp. 533-542, (2015).
Jang, I-K., et al. "Adaptation of cAMP Signaling System in SH-SY5Y Neuroblastoma Cells Following Expression of a Constitutively Active Stimulatory G Protein Alpha, Q227L Gsα," Exp Mol Med, vol. 33, No. 1, pp. 37-45, (2001).
Jiang, X., et al. "Expression and Regulation of mRNA for Distinct Isoforms of CAMP-Specific PDE-4 in Mitogen-Stimulated and Leukemic Human Lymphocytes," Cell Biochem and Biophys, vol. 28, pp. 135-160, (1998).
Marko, D., et al. "Cyclic 3',5'-nucleotide Phosphodiesterases: Potential Targets for Anticancer Therapy," Chem Res Toxicol, vol. 13, pp. 944-948, (2000).
Rowther, F. et al., "Cyclic nucleotide phosphodiesterase-1C (PDE1C) drives cell proliferation, migration and invasion in glioblastoma multiforme cells in vitro," Molecular Carcinogenesis, vol. 55, No. 3, pp. 268-279, (2016).
Rybalkin, S. et al., "Calmodulin-stimulated Cyclic Nucleotide Phosphodiesterase (PDE1C) is Induced in Human Arterial Smooth Muscle Cells of the Synthetic, Proliferative Phenotype," J Clin Invest, vol. 100, No. 10, pp. 2611-2621, (1997).
Stupp, R. et al., "Radiotherapy Plus Concomitant and Adjuvant Temozolomide for Glioblastoma", N Engl J Med, vol. 352, No. 10, pp. 987-996, (2005).
Touat, M., et al. "Glioblastoma Targeted Therapy: Updated Approaches from Recent Biological Insights," Ann. Oncol., vol. 28, No. 7, pp. 1457-1472, (2017).
Watanabe, Y., et al. "Phosphodiesterase 4 Regulates the Migration of B16-F10 Melanoma Cells," Exp Ther Med, vol. 4, pp. 205-210, (2012).

* cited by examiner

COMPOUNDS

CROSS-REFERENCE TO RELATED APPLICATIONS

This application is a U.S. National Stage Application under 35 U.S.C. § 371 of International Application No. PCT/US2020/049141, which was filed on Sep. 3, 2020, which claims priority to and the benefit of U.S. Provisional Application Ser. No. 62/895,477, which was filed on Sep. 3, 2019, the contents of each of which are hereby incorporated by reference in their entireties.

FIELD OF THE INVENTION

The present invention relates to PDE1 inhibitory compounds of Formula Ia as described below, processes for their production, their use as pharmaceuticals and pharmaceutical compositions comprising them. These compounds are useful e.g., in the treatment of diseases involving disorders of the dopamine D1 receptor intracellular pathway, such as, among others, Parkinson's disease, depression, narcolepsy, psychosis, damage to cognitive function, e.g., in schizophrenia, or disorders that may be ameliorated through enhanced progesterone-signaling pathway, e.g., female sexual dysfunction.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), are activated by the $Ca^{2+}$-calmodulin and have been shown to mediate the calcium and cyclic nucleotide (e.g. cAMP and cGMP) signaling pathways. These PDEs are therefore active in stimulated conditions when intra-cellular calcium levels rise, leading to increased hydrolysis of cyclic nucleotides. The three known CaM-PDE genes, PDE1A, PDE1B, and PDE1C, are all expressed in central nervous system tissue. In the brain, the predominant expression of PDE1A is in the cortex and neostriatum, PDE1B is expressed in the neostriatum, prefrontal cortex, hippocampus, and olfactory tubercle, and PDE1C is more ubiquitously expressed.

Cyclic nucleotide phosphodiesterases decrease intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). Phosphorylated DARPP-32 in turn inhibits the activity of protein phosphates-1 (PP-1), thereby increasing the state of phosphorylation of substrate proteins such as progesterone receptor (PR), leading to induction of physiologic responses. Studies in rodents have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, GNP, CNP), endorphin intracellular signaling pathway and progesterone signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity. Chronic elevation in intracellular calcium levels is linked to cell death in numerous disorders, particularly in neurodegenerative diseases such as Alzheimer's, Parkinson's and Huntington's Diseases and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, narcolepsy and cognitive impairment. PDE1 inhibitors are also useful in diseases that may be alleviated by the enhancement of progesterone-signaling such as female sexual dysfunction.

SUMMARY OF THE INVENTION

The inventors have unexpectedly discovered that the major route of metabolism of substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidines of Formula 1a is by way of hydroxylation at the cyclopentyl ring and/or at the phenylamino ring. For example, Compound 1 metabolizes to yield the compounds of Formula M-I, M-II, and M-III, as shown below:

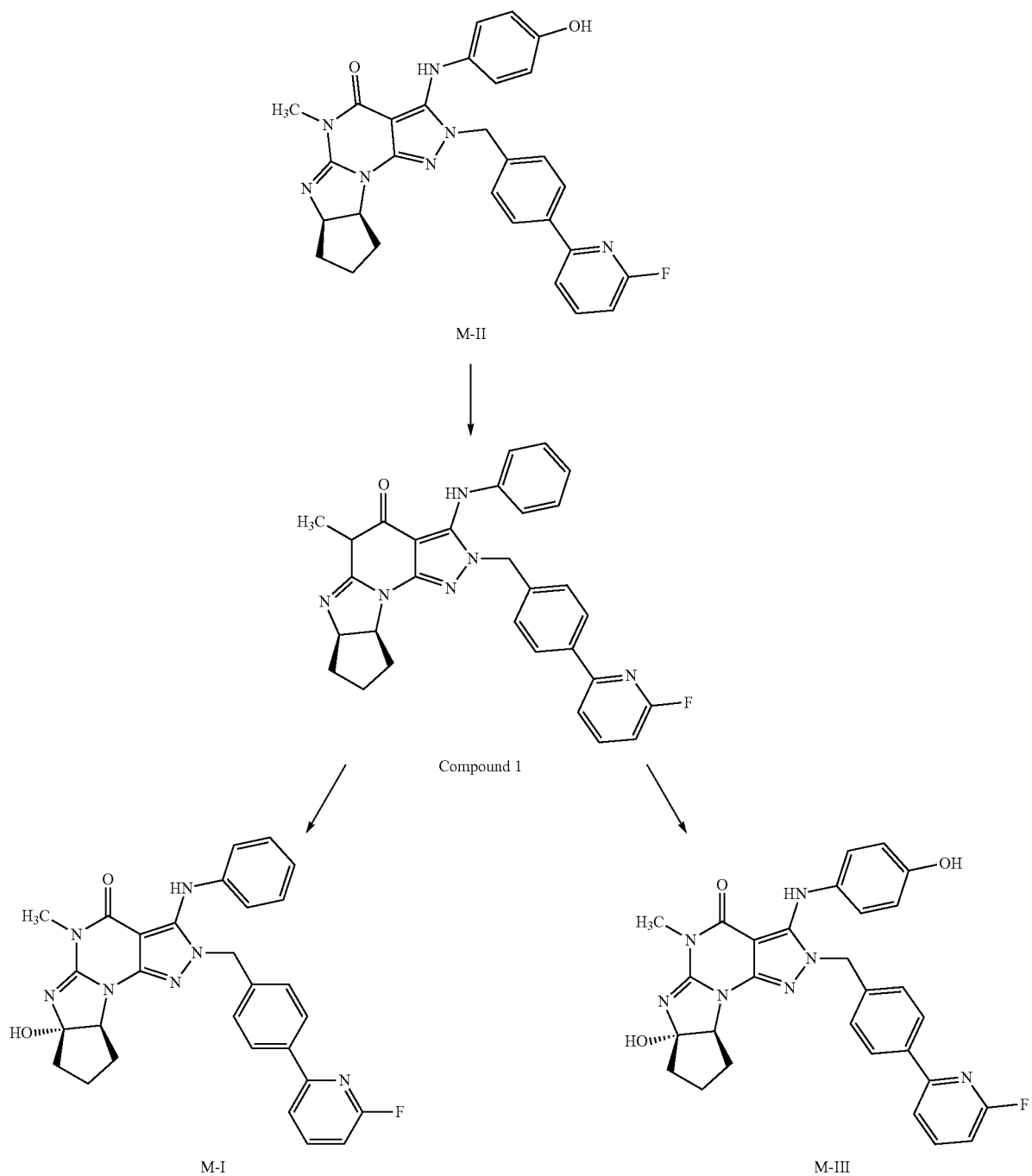

The inventors have further found that the metabolite of Formula M-I accounted for 84% of the total circulating drug related materials in human plasma after oral administration of Compound 1.

Without being bound by theory, the current invention provides compounds which specifically limit and/or prevent metabolism occurring by these pathways. Due to the very similar properties of deuterium ($^2$H) atoms compared to normal hydrogen atoms ($^1$H), drug compounds in which deuterium is substituted for hydrogen are believed to generally have similar biological activity to the non-deuterated analog, but potentially with improved pharmacokinetic properties. The extent to which such a substitution will result in an improvement of pharmacokinetic properties without a too severe loss in pharmacologic activity is variable. Thus, in some circumstances, the resulting deuterated compound only a moderate increase in pharmacokinetic stability, while in other circumstances, the resulting deuterated compound may have significantly improved stability. Moreover, it may be difficult to predict with certainty the effects of simultaneous deuterium substitutions. These may or may not result in additive (synergistic) improvement in metabolic stability.

In various embodiments, the invention provides various PDE1 inhibitory compounds for use in treatment of any one or more of the following conditions:

(i) Neurodegenerative diseases, including Parkinson's disease, restless leg, tremors, dyskinesias, Huntington's disease, Alzheimer's disease, and drug-induced movement disorders;
(ii) Mental disorders, including depression, attention deficit disorder, attention deficit hyperactivity disorder, bipolar illness, anxiety, sleep disorders, e.g., narcolepsy, cognitive impairment, e.g., cognitive impairment of schizophrenia, dementia, Tourette's syndrome, autism, fragile X syndrome, psychostimulant withdrawal, and drug addiction;
(iii) Circulatory and cardiovascular disorders, including cerebrovascular disease, stroke, congestive heart disease, hypertension, pulmonary hypertension, e.g., pulmonary arterial hypertension, and sexual dysfunction, including cardiovascular diseases and related disorders as described in International Application No. PCT/US2014/16741, the contents of which are incorporated herein by reference;
(iv) Respiratory and inflammatory disorders, including asthma, chronic obstructive pulmonary disease, and allergic rhinitis, as well as autoimmune and inflammatory diseases;
(v) Diseases that may be alleviated by the enhancement of progesterone-signaling such as female sexual dysfunction;
(vi) A disease or disorder such as psychosis, glaucoma, or elevated intraocular pressure;
(vii) Traumatic brain injury;
(viii) Cancers or tumors, e.g., brain tumors, a glioma (e.g., ependymoma, astrocytoma, oligodendrogliomas, brain stem glioma, optic nerve glioma, or mixed gliomas, e.g., oligoastrocytomas), an astrocytoma (e.g., glioblastoma multiforme), osteosarcoma, melanoma, leukemia, neuroblastoma or leukemia;
(ix) Renal disorders, e.g., kidney fibrosis, chronic kidney disease, renal failure, glomerulosclerosis and nephritis;
(x) Any disease or condition characterized by low levels of cAMP and/or cGMP (or inhibition of cAMP and/or cGMP signaling pathways) in cells expressing PDE1; and/or
(xi) Any disease or condition characterized by reduced dopamine D1 receptor signaling activity, comprising administering an effective amount of a Compound of the Invention, e.g., a compound according to any of Formula Ia or 1.1-1.26, in free or pharmaceutically acceptable salt or prodrug form, to a human or animal patient in need thereof.

In various embodiments, the invention provides a method of preventing the formation of metabolites of the following compound:

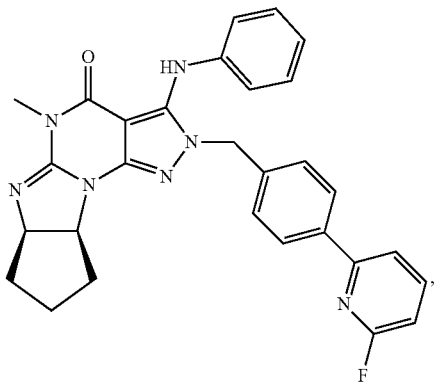 [SMILES: CN1C(=O)c2c(nn(Cc3ccc(-c4cccc(F)n4)cc3)c2Nc2ccccc2)N2C1=N[C@@H]1CCC[C@@H]12]

the method comprising deuterating the PDE1 inhibitor to block the formation of one or more metabolites.

Further embodiments of the invention are set forth or evident from the detailed description below and the examples herein.

DETAILED DESCRIPTION

Compounds of the Present Disclosure

In one embodiment, the present disclosure provides that the PDE1 inhibitors for use in the methods as described herein are Formula 1a:

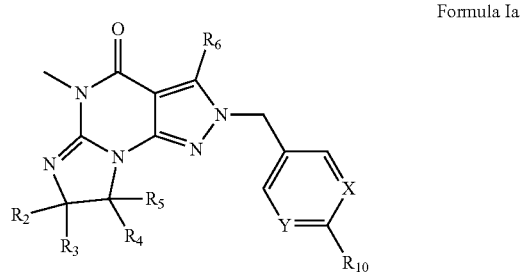

Formula Ia wherein
(i) $R_2$ and $R_5$ are independently H, D or hydroxy and $R_3$ and $R_4$ together form a tri- or tetra-methylene bridge [pref. with the carbons carrying $R_3$ and $R_4$ having the R and S configuration respectively]; or $R_2$ and $R_3$ are each methyl and $R_4$ and $R_5$ are each H; or $R_2$, $R_4$ and $R_5$ are H and $R_3$ is isopropyl [pref. the carbon carrying $R_3$ having the R configuration];
(ii) $R_6$ is (optionally halo-substituted or hydroxy-substituted) phenylamino, (optionally halo-substituted or hydroxy-substituted) benzylamino, $C_{1-4}$alkyl, or $C_{1-4}$-alkyl sulfide; for example, phenylamino or 4-fluorophenylamino;
(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl (for example 6-fluoropyrid-2-yl), or thiadiazolyl (e.g., 1,2,3-thiadiazol-4-yl); and X and Y are independently C or N,
in free, pharmaceutically acceptable salt or prodrug form, including its enantiomers, diastereoisomers and racemates.

The invention further provides compounds of Formula Ia as follows:
1.1 A compound according to Formula 1a, wherein $R_2$ and $R_5$ are independently D or hydroxy; or $R_6$ is hydroxy-substituted phenylamino or hydroxy-substituted benzylamino.
1.2 A compound according to Formula Ia or 1.1, wherein $R_2$ and $R_5$ are independently D or hydroxy.
1.3 A compound according to Formula Ia or 1.1-1.2, wherein $R_6$ is hydroxy-substituted phenylamino or hydroxy-substituted benzylamino.
1.4 A compound according to Formula Ia or 1.1-1.3, wherein $R_6$ is hydroxy-substituted phenylamino.
1.5 A compound according to Formula Ia or 1.1-1.3, wherein $R_6$ is hydroxy-substituted benzylamino.
1.6 A compound according to Formula Ia a or 1.1-1.5, wherein $R_2$ and $R_5$ are independently H, D or hydroxy and $R_3$ and $R_4$ together form a tri- or tetra-methylene bridge [pref. with the carbons carrying $R_3$ and $R_4$ having the R and S configuration respectively].

1.7 A compound according to Formula 1a or 1.1-1.6, wherein at least one of $R_2$ and $R_5$ are D.
1.8 A compound according to Formula 1a or 1.1-1.7, wherein $R_2$ and $R_5$ are both D.
1.9 A compound according to Formula 1a or 1.1-1.8, wherein $R_2$ and $R_5$ are both D and $R_3$ and $R_4$ together form a tri- or tetra-methylene bridge.
1.10 A compound according to Formula 1a or 1.1-1.5, wherein at least one of $R_2$ and $R_5$ are hydroxy.
1.11 A compound according to Formula 1a, 1.1-1.5 or 1.10, wherein at least one of $R_2$ and $R_5$ are hydroxy and $R_3$ and $R_4$ together form a tri- or tetra-methylene bridge.
1.12 A compound according to Formula 1a, 1.1-1.5 or 1.10-1.11, wherein $R_2$ is hydroxy.
1.13 A compound according to Formula 1a, 1.1-1.5 or 1.0-1.11, wherein $R_5$ is hydroxy.
1.14 A compound according to Formula 1a or 1.1-1.11, wherein $R_{10}$ is pyridyl.
1.15 A compound according to Formula 1a or 1.1-1.12, wherein $R_{10}$ is halo- or hydroxy-substituted pyridyl.
1.16 A compound according to Formula 1a or 1.1-1.12, wherein $R_{10}$ is halo-substituted pyridyl.
1.17 A compound according to Formula 1a or 1.1-1.12, wherein $R_{10}$ is hydroxy-substituted pyridyl.
1.18 A compound according to Formula 1a or 1.1-1.12, wherein $R_{10}$ is 6-fluoropyrid-2-yl.
1.19 A compound according to Formula 1a or 1.1-1.18, wherein X and Y are both C.
1.20 A compound according to Formula 1a or 1.1-1.19, wherein the PDE1 inhibitor is a compound according to the following:

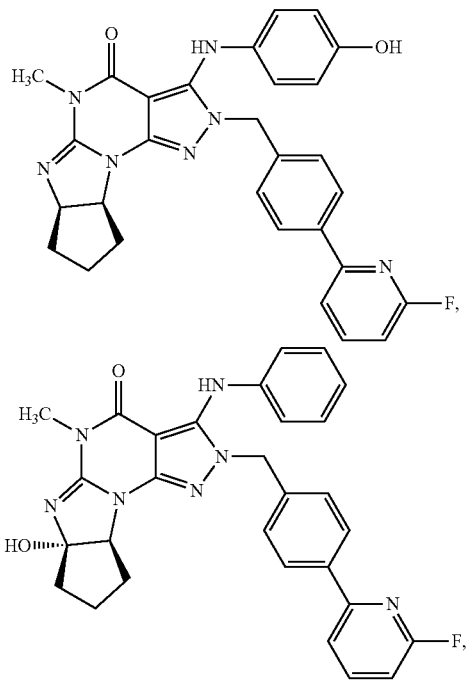

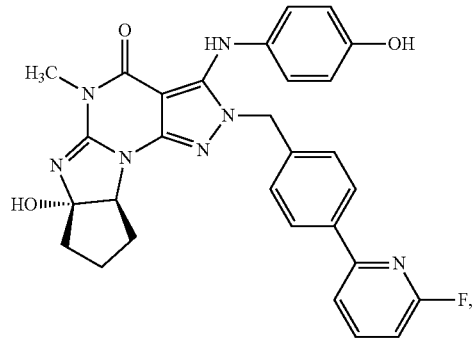

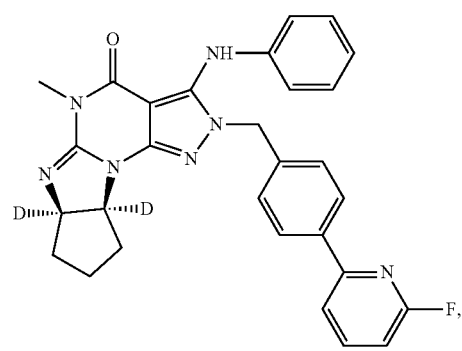

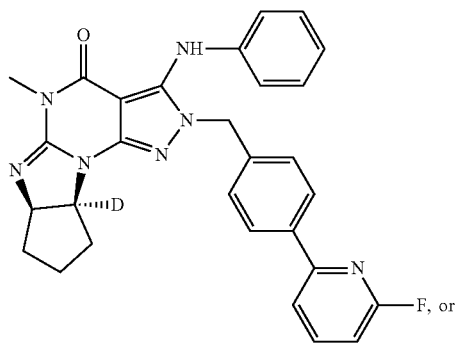

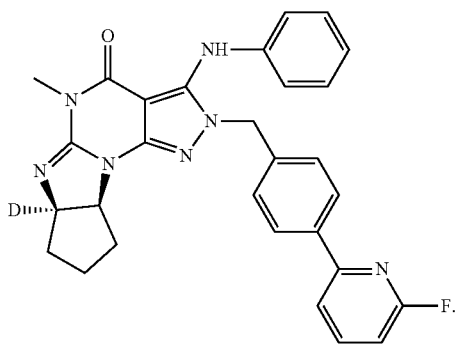

1.21 A compound according to Formula 1a or 1.1-1.20, wherein the PDE1 inhibitor is a compound according to the following:

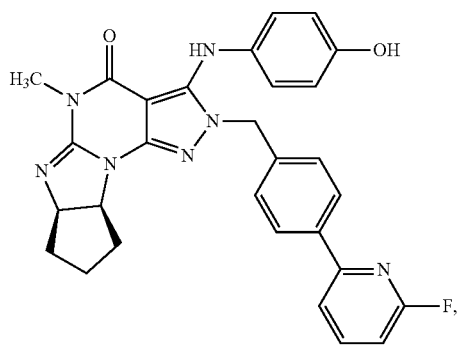
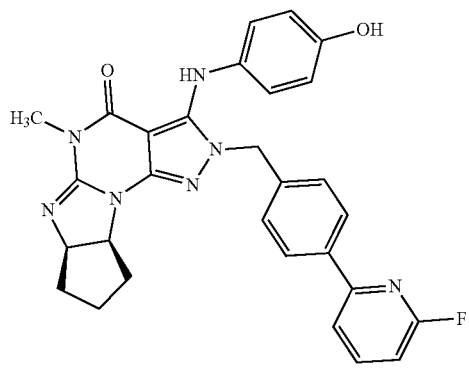
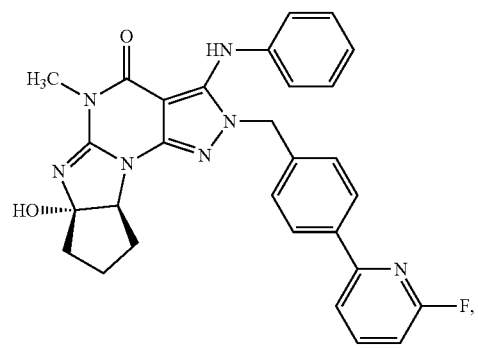
,
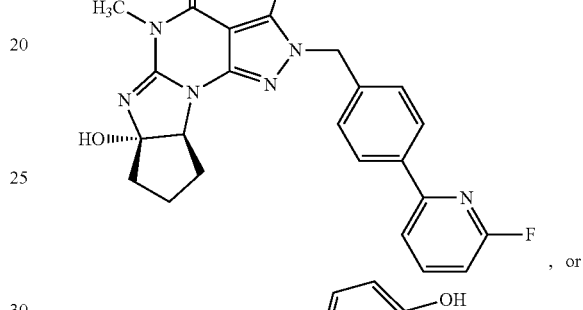
, or
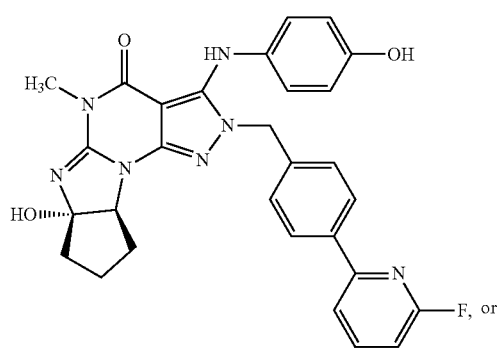
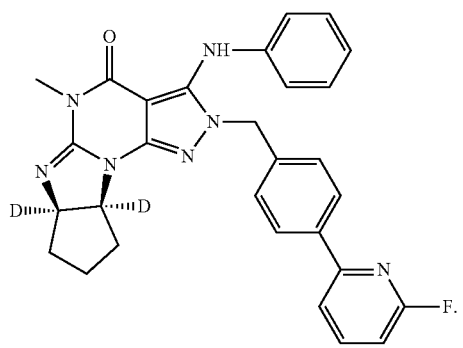
1.23 A compound according to Formula 1a or 1.1-1.22, wherein the PDE1 inhibitor is a compound according to the following:
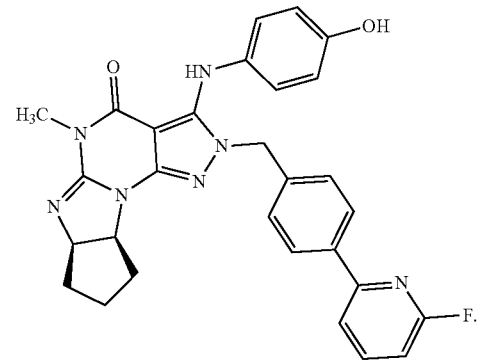 [SMILES: CN1C(=O)c2c(nn(Cc3ccc(-c4cccc(F)n4)cc3)c2Nc2ccc(O)cc2)N2C1=N[C@@H]1CCC[C@@H]12]
.
1.22 A compound according to Formula 1a or 1.1-1.21, wherein the PDE1 inhibitor is a compound according to the following:
1.24 A compound according to Formula 1a or 1.1-1.22, wherein the PDE1 inhibitor is a compound according to the following:

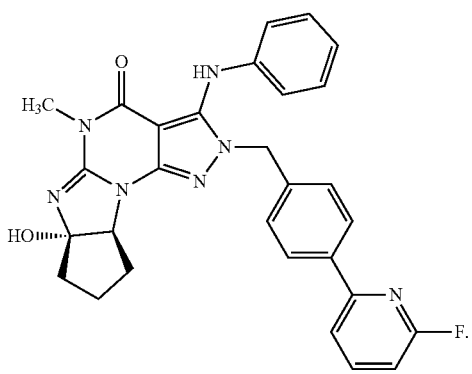 [SMILES: CN1C(=O)c2c(nn(Cc3ccc(-c4cccc(F)n4)cc3)c2Nc2ccccc2)N2C1=N[C@]1(O)CCC[C@H]21]

1.25 A compound according to Formula 1a or 1.1-1.22, wherein the PDE1 inhibitor is a compound according to the following:

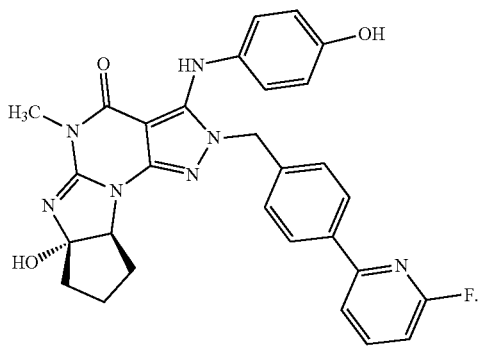 [SMILES: CN1C(=O)c2c(nn(Cc3ccc(-c4cccc(F)n4)cc3)c2Nc2ccc(O)cc2)N2C1=N[C@]1(O)CCC[C@H]21]

1.26 A compound according to Formula 1a or 1.1-1.21, wherein the PDE1 inhibitor is a compound according to the following:

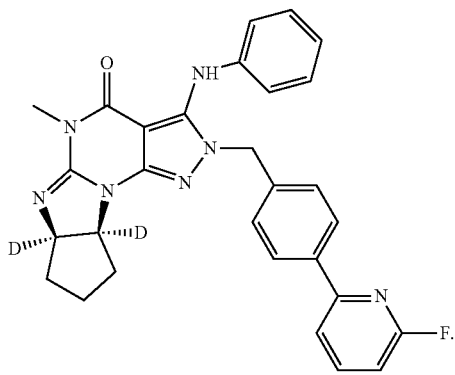 [SMILES: [2H][C@@]12CCC[C@]1([2H])N1C(=N2)N(C)C(=O)c2c1nn(Cc1ccc(-c3cccc(F)n3)cc1)c2Nc1ccccc1]

1.27 Any foregoing compound, wherein the compound is deuterated, e.g., wherein the deuterium:protium ratio at a specified position in the molecule is significantly higher, e.g., at least 2×, for example at least 10× higher, than the natural isotope ratios.

In another embodiment, the present disclosure further provides for a radiolabeled PDE1 inhibitor [Compound 2], e.g., for use in the methods as described herein, according to Formula 1a or 1.1-1.26.

2.1 Compound 2, wherein at least one carbon atom substituted with Carbon-14 ($[^{14}C]$).

2.2 Any of the preceding Compounds, wherein one carbon atom substituted with Carbon-14 ($[^{14}C]$).

2.3 Any of the preceding Compounds, wherein the radiolabeled PDE1 inhibitor is a compound according to the following:

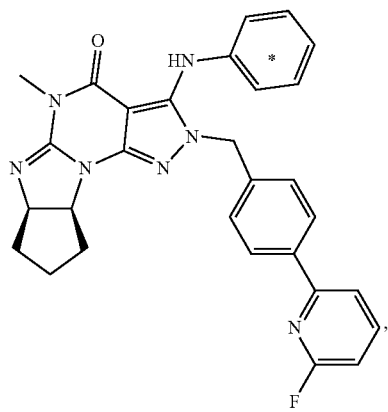 [SMILES: CN1C(=O)c2c(nn(Cc3ccc(-c4cccc(F)n4)cc3)c2Nc2ccccc2)N2C1=N[C@@H]1CCC[C@@H]12]

or a pharmaceutically acceptable salt thereof.

2.4 Compound 2.3, wherein the compound is in salt form.
2.5 Compound 2.4, wherein the compound is in phosphate salt form.
2.6 Compound 2.5, wherein the compound is in monophosphate salt form.

In one embodiment, selective PDE1 inhibitors of the preceding formula (e.g., Formula Ia or 1.1-1.26) are compounds that inhibit phosphodiesterase-mediated (e.g., PDE1-mediated, especially PDE1B-mediated) hydrolysis of cGMP, e.g., the preferred compounds have an $IC_{50}$ of less than 1 μM, preferably less than 500 nM, preferably less than 50 nM, and preferably less than 5 nM in an immobilized-metal affinity particle reagent PDE assay, in free or salt form.

If not otherwise specified or clear from context, the following terms herein have the following meanings:

"Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

"Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

"Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

"Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

"Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

It is intended that wherein the substituents end in "ene", for example, alkylene, phenylene or arylalkylene, said substituents are intended to bridge or be connected to two other substituents. Therefore, methylene is intended to be —$CH_2$— and phenylene intended to be —$C_6H_4$— and arylalkylene is intended to be —$C_6H_4$—$CH_2$— or —$CH_2$—$C_6H_4$—.

Compounds of the Invention, e.g., substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., Compounds of Formula Ia, may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

In another embodiment, the invention further provides a pharmaceutical composition comprising a Compound of the Invention, in free or pharmaceutically acceptable salt form, in admixture with a pharmaceutically acceptable carrier, for use in the treatment of a disease or disorder mediated by PDE1.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)-$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

In another embodiment, the invention further provides a pharmaceutical composition comprising a Compound of the Invention, in free, pharmaceutically acceptable salt or prodrug form, in admixture with a pharmaceutically acceptable carrier, for use in the treatment of a disease or disorder mediated by PDE1.

Methods of Making Compounds of the Invention

The compounds of the Invention and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds.

Various starting materials and/or Compounds of the Invention may be prepared using methods described in US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138, and U.S. Pat. No. 9,073,936, the contents of each of which herein are hereby incorporated by reference in their entireties.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-radioactive). Examples of known stable isotopes include, but not limited to, deuterium, $^{13}$C, $^{15}$N, $^{18}$O. Alternatively, unstable isotopes, which are radioactive isotopes which contain additional neutrons compared to the abundant nuclides of the same species (i.e., element), e.g., 123I, $^{131}$I, $^{125}$I, $^{11}$C, $^{18}$F, may replace the corresponding abundant species of I, C and F. Another example of useful isotope of the compound of the invention is the $^{11}$C isotope. These radio isotopes are useful for radio-imaging and/or pharmacokinetic studies of the compounds of the invention.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks. Solvent mixture compositions are given as volume percentages or volume ratios. In cases where the NMR spectra are complex, only diagnostic signals are reported.

Methods of using Compounds of the Invention

The Compounds of the Invention are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1, thereby increasing intracellular levels of cAMP and cGMP, the Compounds of the Invention potentiate the activity of cyclic nucleotide synthesis inducers.

The invention provides methods of treatment of any one or more of the following conditions:

(i) Neurodegenerative diseases, including Parkinson's disease, restless leg, tremors, dyskinesias, Huntington's disease, Alzheimer's disease, and drug-induced movement disorders;

(ii) Mental disorders, including depression, attention deficit disorder, attention deficit hyperactivity disorder, bipolar illness, anxiety, sleep disorders, e.g., narcolepsy, cognitive impairment, e.g., cognitive impairment of schizophrenia, dementia, Tourette's syndrome, autism, fragile X syndrome, psychostimulant withdrawal, and drug addiction;

(iii) Circulatory and cardiovascular disorders, including cerebrovascular disease, stroke, congestive heart disease, hypertension, pulmonary hypertension, e.g., pulmonary arterial hypertension, and sexual dysfunction, including cardiovascular diseases and related disorders as described in International Application No. PCT/US2014/16741, the contents of which are incorporated herein by reference;

(iv) Respiratory and inflammatory disorders, including asthma, chronic obstructive pulmonary disease, and allergic rhinitis, as well as autoimmune and inflammatory diseases;

(v) Diseases that may be alleviated by the enhancement of progesterone-signaling such as female sexual dysfunction;

(vi) A disease or disorder such as psychosis, glaucoma, or elevated intraocular pressure;

(vii) Traumatic brain injury;

(viii) Any disease or condition characterized by low levels of cAMP and/or cGMP (or inhibition of cAMP and/or cGMP signaling pathways) in cells expressing PDE1; and/or (ix) Any disease or condition characterized by reduced dopamine D1 receptor signaling activity, comprising administering an effective amount of a Compound of the Invention, e.g., a compound according to any of Formula Ia or 1.1-1.26, in free or pharmaceutically acceptable salt or prodrug form, to a human or animal patient in need thereof.

The Compounds of the Invention are useful in the treatment of inflammatory diseases or conditions, particularly neuroinflammatory diseases or conditions. Therefore, administration or use of a preferred PDE1 inhibitor as described herein, e.g., a PDE1 inhibitor as hereinbefore described, e.g., a Compound of Formula Ia, provides a means to regulate inflammation (e.g., prevent, reduce, and/or reverse neuroinflammation, and diseases or disorders related to neuroinflammation), and in certain embodiments provide a treatment for various inflammatory diseases and disorders. In certain embodiments, the inflammatory disease or condition is selected from:

a. neurodegenerative conditions such as Alzheimer's disease (AD), Parkinson's disease (PD), amyotrophic lateral sclerosis (ALS), and demyelinating conditions, e.g., multiple sclerosis (MS), and prion diseases;

b. stroke, cardiac arrest, hypoxia, intracerebral hemorrhage or traumatic brain injury;

c. conditions characterized by abnormal neurotransmitter production and/or response, including depression, schizophrenia, post-traumatic stress disorder, anxiety, attention deficit disorder, and bipolar disease; e.g., wherein any of the foregoing are associated with neuroinflammation; and d. chronic CNS infections, e.g., Lyme disease or CNS infection consequent to an immunosuppressive condition, e.g., HIV-dementia;

e. neuroinflammation consequent to chemotherapy;

comprising administering an effective amount of a PDE1 inhibitor of the current invention (e.g., a PDE1 inhibitor of Formula Ia as herein described), e.g., an amount effective to (i) reduce or inhibit activation of M1 microglia, and/or (ii) and amount effective to reduce levels of one or more pro-inflammatory cytokines (e.g., IL1β, TNF-α, and Ccl2, or combination thereof); to a patient in need thereof.

The Compounds of the Invention are useful in the treatment of cancers or tumors, e.g., in the inhibition of the proliferation of cancerous or tumorous cells. Therefore, administration or use of a preferred PDE1 inhibitor as described herein, e.g., a PDE1 inhibitor as hereinbefore described, e.g., a Compound of Formula Ia, in the treatment or prevention of a cancer or tumor.

It is contemplated that the compounds of the present disclosure can be used in the treatment of a tumor or cancer selected from one or more of acoustic neuroma, astrocytoma, chordoma, lymphoma (e.g., CNS lymphoma, Hodgkin's lymphoma or non-Hodgkin's lymphoma), craniopharyngioma, gliomas (e.g., Brain stem glioma, ependymoma, mixed glioma, optic nerve glioma), subependymoma, medulloblastoma, meningioma, metastatic brain tumors, oligodendroglioma, pituitary tumors, primitive neuroectodermal (PNET), schwannoma, adenomas (e.g., basophilic adenoma, eosinophilic adenoma, chromophobe adenoma, parathyroid adenoma, islet adenoma, fibroadenoma), fibroids (fibrous histiocytoma), fibromas, hemangiomas, lipomas (e.g., angiolipoma, myelolipoma, fibrolipoma, spindle cell lipoma, hibernoma, atypical lipoma), myxoma, osteoma, preleukemias, rhabdomyoma, papilloma, seborrheic keratosis, skin adnexal tumors, hepatic adenomas, renal tubular adenoma, bile duct adenoma, transitional cell papilloma, hydatidiform moles, ganglioneuroma, meningioma, neurilemmoma, neurofibroma, C cell hyperplasia, pheochromocytoma, insulinoma, gastrinoma, carcinoids, chemodectoma, paraganglioma, nevus, actinic keratosis, cervical dysplasia, metaplasia (e.g., metaplasia of the lung), leukoplakia, hemangioma, lymphangioma, carcinoma (e.g., squamous cell carcinoma, epidermoid carcinoma, adenocarcinoma, hepatoma, hepatocellular carcinoma, renal cell carcinoma, cholangiocarcinoma, transitional cell carcinoma, embryonal cell carcinoma, parathyroid carcinoma, medullary carcinoma of thyroid, bronchial carcinoid, oat cell carcinoma, islet cell carcinoma, malignant carcinoid, Merkel cell carcinoma), sarcoma (e.g., fibrosarcoma, myxosarcoma, liposarcoma, chondrosarcoma, osteosarcoma, malignant fibrous histiocytoma, hemangiosarcoma, angiosarcoma, lymphangiosarcoma, leiomyosarcoma, rhabdomyosarcoma, neurofibrosarcoma), blastoma (e.g., medulloblastoma and glioblastoma, types of brain tumor, retinoblastoma, a tumor in the retina of the eye, osteoblastoma, bone tumors, neuroblastoma), germ cell tumor, mesothelioma, malignant skin adnexal tumors, hypernephroma, seminoma, glioma, malignant meningioma, malignant schwannoma, malignant pheochromocytoma, malignant paraganglioma, melanoma, Merkel cell neoplasm, cystosarcoma phylloides, or Wilms tumor. Further treatments include lung cancer, pancreatic cancer, prostate cancer, urothelial cancer, cancers of the head and neck, or leukemia (e.g., a lymphocytic leukemia or a myelogenous leukemia), colon cancer (e.g., colorectal cancer) and cancers of the kidney, ureter, bladder or urethra.

The current invention also provides compounds which specifically limit and/or prevent metabolism of PDE1 inhibitors, as well as related methods. Therefore, in one embodiment the invention provides a method (Method 1) of inhibiting the metabolism of a PDE1 inhibitor, e.g. a PDE1 inhibitor according to Formula 1a or 1.1-1.26, the method comprising deuterating the PDE1 inhibitor to block the formation of one or more metabolites.

1.1 Method 1, wherein the PDE1 inhibitor is a compound according to the following formula:

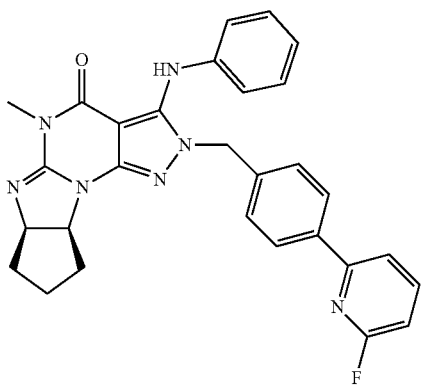 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

1.2. Any of the preceding Methods, wherein deuterating the PDE1 inhibitor comprises reacting:

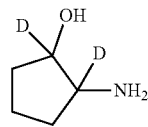

with

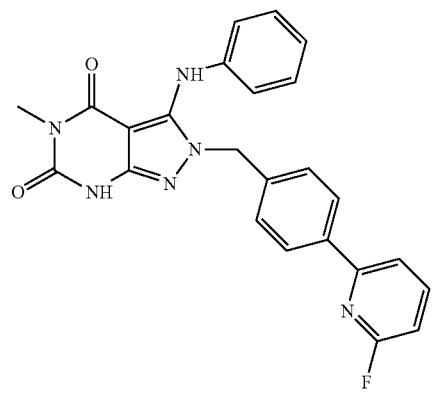 [SMILES: Cn1c(=O)[nH]c2nn(Cc3ccc(-c4cccc(F)n4)cc3)c(Nc3ccccc3)c2c1=O]

to form

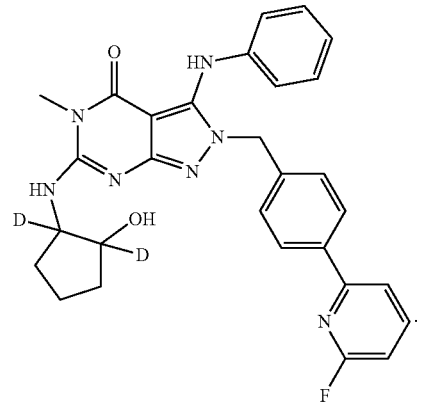 [SMILES: [2H]C1(O)CCCC1([2H])Nc1nc2nn(Cc3ccc(-c4cccc(F)n4)cc3)c(Nc3ccccc3)c2c(=O)n1C]

1.3. The preceding Method, wherein deuterating the PDE1 inhibitor comprises reacting:

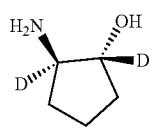

with

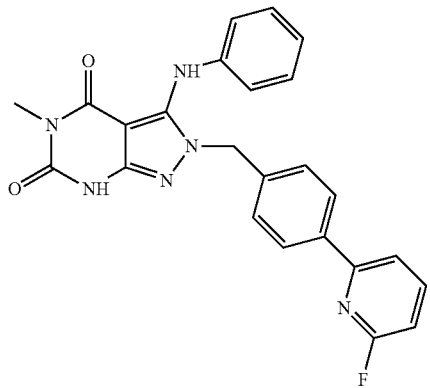 [SMILES: Cn1c(=O)[nH]c2nn(Cc3ccc(-c4cccc(F)n4)cc3)c(Nc3ccccc3)c2c1=O]

to form

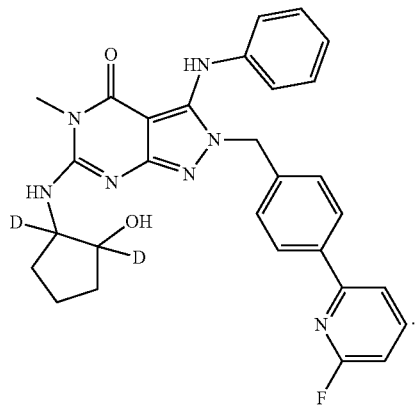 [SMILES: [2H]C1(O)CCCC1([2H])Nc1nc2nn(Cc3ccc(-c4cccc(F)n4)cc3)c(Nc3ccccc3)c2c(=O)n1C]

1.4. The preceding Method, wherein the reaction is carried out in benzotriazol-1-yloxytris(dimethylamino)phosphonium hexafluorophosphate, THF and 1,8-Diazabicyclo[5.4.0]undec-7-ene.

1.5. The two preceding Methods, wherein the

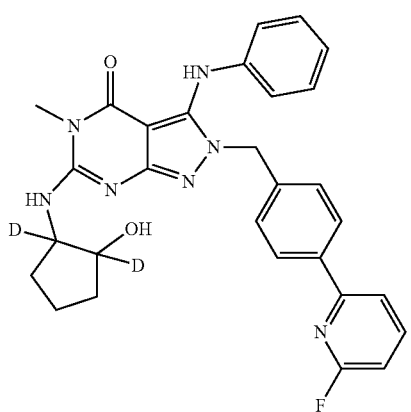 [SMILES: [2H]C1(O)CCCC1([2H])Nc1nc2nn(Cc3ccc(-c4cccc(F)n4)cc3)c(Nc3ccccc3)c2c(=O)n1C]

is reacted with thionyl chloride in THF to form

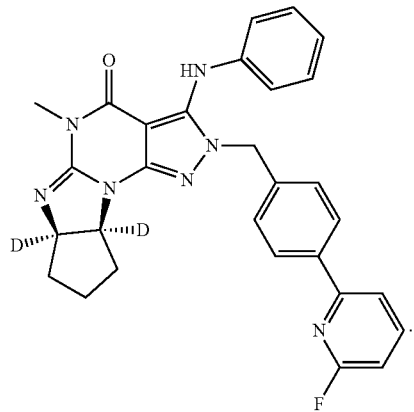 [SMILES: [2H][C@@]12CCC[C@]1([2H])N1C(=N2)N(C)C(=O)c2c1nn(Cc1ccc(-c3cccc(F)n3)cc1)c2Nc1ccccc1]

1.6. Method 1.2, wherein the reaction is carried out in benzotriazol-1-yloxytris(dimethylamino)phosphonium hexafluorophosphate, THF and 1,8-Diazabicyclo[5.4.0]undec-7-ene.

1.7. Method 1.2 or 1.6, wherein the

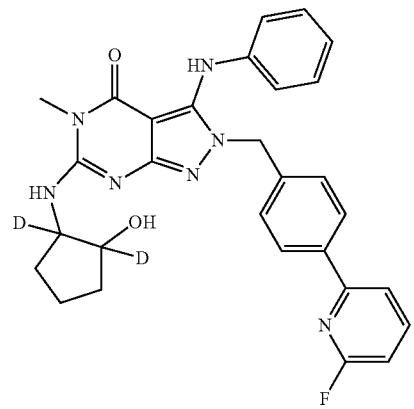 [SMILES: [2H]C1(O)CCCC1([2H])Nc1nc2nn(Cc3ccc(-c4cccc(F)n4)cc3)c(Nc3ccccc3)c2c(=O)n1C]

is reacted with thionyl chloride in THF to form the following product:

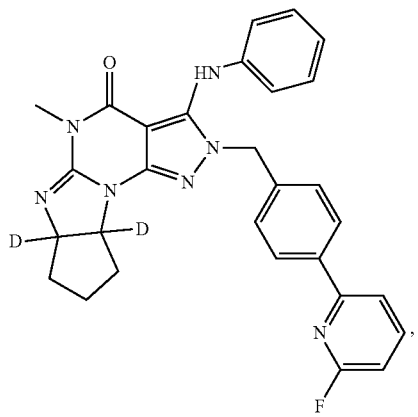 [SMILES: [2H]C12CCCC1([2H])N1C(=N2)N(C)C(=O)c2c1nn(Cc1ccc(-c3cccc(F)n3)cc1)c2Nc1ccccc1]

and subjecting the product to chiral column separation to obtain:

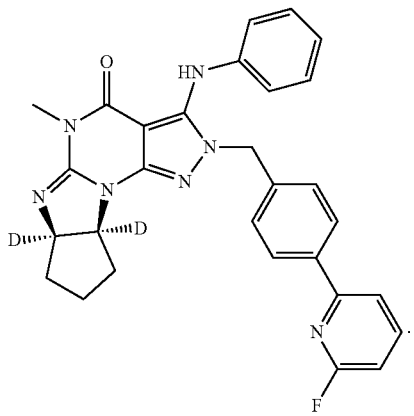 [SMILES: [2H][C@@]12CCC[C@]1([2H])N1C(=N2)N(C)C(=O)c2c1nn(Cc1ccc(-c3cccc(F)n3)cc1)c2Nc1ccccc1]

The phrase "Compounds of the Invention" or "PDE 1 inhibitors of the Invention", or like terms, encompasses any and all of the compounds disclosed herewith, e.g., a Compound of Formula Ia or 1.1-1.26.

The words "treatment" and "treating" are to be understood accordingly as embracing prophylaxis and treatment or amelioration of symptoms of disease as well as treatment of the cause of the disease.

For methods of treatment, the word "effective amount" is intended to encompass a therapeutically effective amount to treat or mitigate a specific disease or disorder, and/or a symptom thereof, and/or to inhibit PDE1 expression in a patient or subject.

The term "patient" includes a human or non-human (i.e., animal) patient. In a particular embodiment, the invention encompasses both humans and nonhuman animals. In another embodiment, the invention encompasses nonhuman animals. In other embodiments, the term encompasses humans.

The term "comprising" as used in this disclosure is intended to be open-ended and does not exclude additional, unrecited elements or method steps.

Compounds of the Invention, e.g., Formula Ia and 1.1-1.26 as hereinbefore described, in free or pharmaceutically acceptable salt form, may be used as a sole therapeutic agent, but may also be used in combination or for co-administration with other active agents.

For example, in certain embodiments, the Compounds of the Invention, e.g., Formula Ia or 1.1-1.26 as hereinbefore described, in free or pharmaceutically acceptable salt form, may be administered in combination (e.g. administered sequentially or simultaneously or within a 24 hour period) with other active agents, e.g., with one or more antidepressant agents, e.g., with one or more compounds in free or pharmaceutically acceptable salt form, selected from selective serotonin reuptake inhibitors (SSRIs) serotonin-norepinephrine reuptake inhibitors (SNRIs), c) tricyclic antidepressants (TCAs), and atypical antipsychotics.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg (depending on the drug to be administered and the condition to be treated, for example in the case of Compound 214, 0.5 to 25 mg, e.g., 1 to 10 mg, per diem, e.g., in monophosphate salt form, for treatment of PDE1-mediated conditions), conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg (e.g., 1, 2.5, 5, 10, or 20 mg) of a Compound of the Invention, e.g., together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

Example 1

Measurement of PDE1B Inhibition In Vitro Using IMAP Phosphodiesterase Assay Kit

Phosphodiesterase I B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, CA) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Amp). Inhibition of phosphodiesterase, therefore, is detected as a decrease in Amp.

Enzyme Assay

Materials: All chemicals are available from Sigma-Aldrich (St. Louis, MO) except for IMAP reagents (reaction buffer, binding buffer, FL-GMP and IMAP beads), which are available from Molecular Devices (Sunnyvale, CA).

Assay: The following phosphodiesterase enzymes may be used: 3',5'-cyclic-nucleotide-specific bovine brain phosphodiesterase (Sigma, St. Louis, MO) (predominantly PDE1B) and recombinant full length human PDE1 A and PDE1B (r-hPDE1 A and r-hPDE1B respectively) which may be produced e.g., in HEK or SF9 cells by one skilled in the art. The PDE1 enzyme is reconstituted with 50% glycerol to 2.5 U/ml. One unit of enzyme will hydrolyze 1.0 μm of 3',5'-cAMP to 5'-AMP per min at pH 7.5 at 30° C. One part enzyme is added to 1999 parts reaction buffer (30 μM $CaCl_2$, 10 U/ml of calmodulin (Sigma P2277), 10 mM Tris-HCl pH 7.2, 10 mM $MgCl_2$, 0.1% BSA, 0.05% $NaN_3$) to yield a final concentration of 1.26 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μL of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, CT) to measure the fluorescence polarization (Amp).

A decrease in GMP concentration, measured as decreased Amp, is indicative of inhibition of PDE activity. IC50 values are determined by measuring enzyme activity in the presence of 8 to 16 concentrations of compound ranging from 0.0037 nM to 80,000 nM and then plotting drug concentration versus AmP, which allows IC50 values to be estimated using nonlinear regression software (XLFit; IDBS, Cambridge, MA).

Compounds of the present disclosure are tested in an assay as described or similarly described herein for PDE1 inhibitory activity. For example, Compounds 1, 2 and 3 are identified as metabolites of a specific PDE1 inhibitor having the following structures:

Compound 1

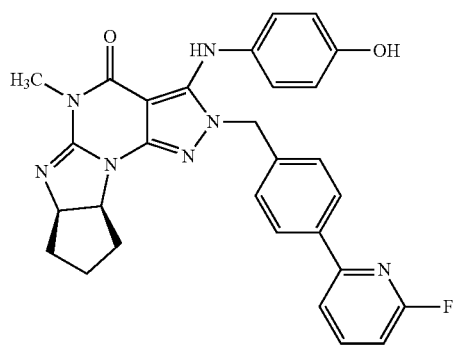

Compound 2

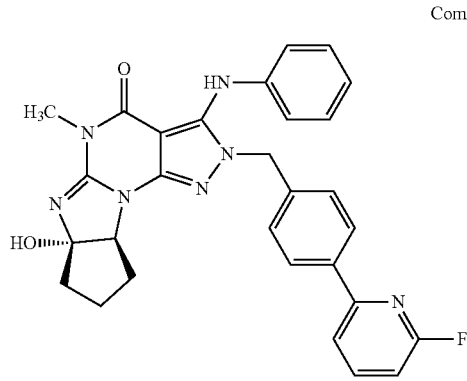

Compound 3

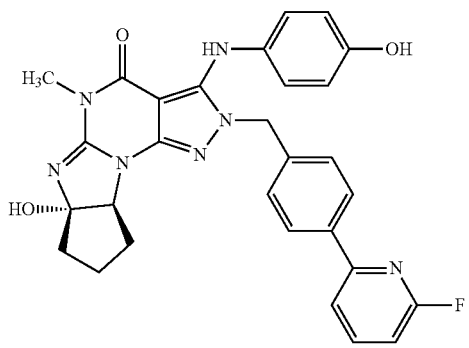

These compounds have efficacy at nanomolar or sub-nanomolar levels vs PDE1 and generally high selectivity over other PDE families, as depicted on the following table:

| PDE Target | Compound 1 IC$_{50}$ (nM) | Compound 2 IC$_{50}$ (nM) | Compound 3 IC$_{50}$ (nM) |
|---|---|---|---|
| PDE1A | 1.3 | 0.042 | 6.3 |
| PDE1B | 29.0 | 0.015 | 1.4 |
| PDE1C | 1.3 | 0.042 | 5.4 |
| hPDE2A | >100,000 | ~10,000 | 73,401 |
| hPDE3B | 49,692 | ~10,000 | 20,894 |
| hPDE4A1A | 3,657 | 22 | 840 |
| r-bovine PDE5 | 2,478 | 3.1 | 156 |
| bovine PDE6 | 4,339 | 34 | 294 |
| hPDE7B | 6,608 | 118 | 1,244 |
| hPDE8A | 4,175 | 418 | 3,421 |
| hPDE9A | >100,000 | >10000 | >100,000 |
| hPDE10A | >100,000 | >10000 | 67,380 |
| hPDE11 | 5,438 | 454 | 396 |

Example 2

Synthesis of (6aS,9aR)-6a,9a-dideuterio-2-(4-(6-fluoropyridin-2-yl)benzyl)-5-methyl-3-(phenylamino)-5,6a,7,8,9,9a-hexahydrocyclopenta[4,5]imidazo[1,2-a]pyrazolo[4,3-e]pyrimidin-4(2H)-one The title compound is generally carried out according to Scheme 1.

Scheme 1

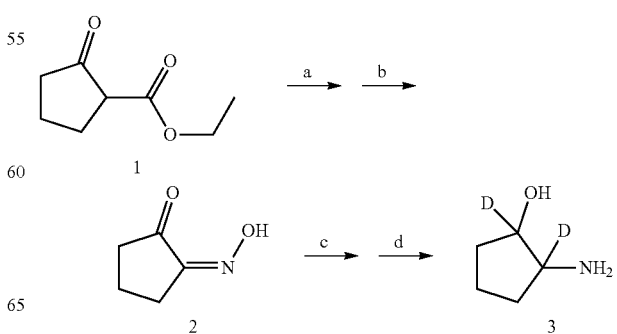

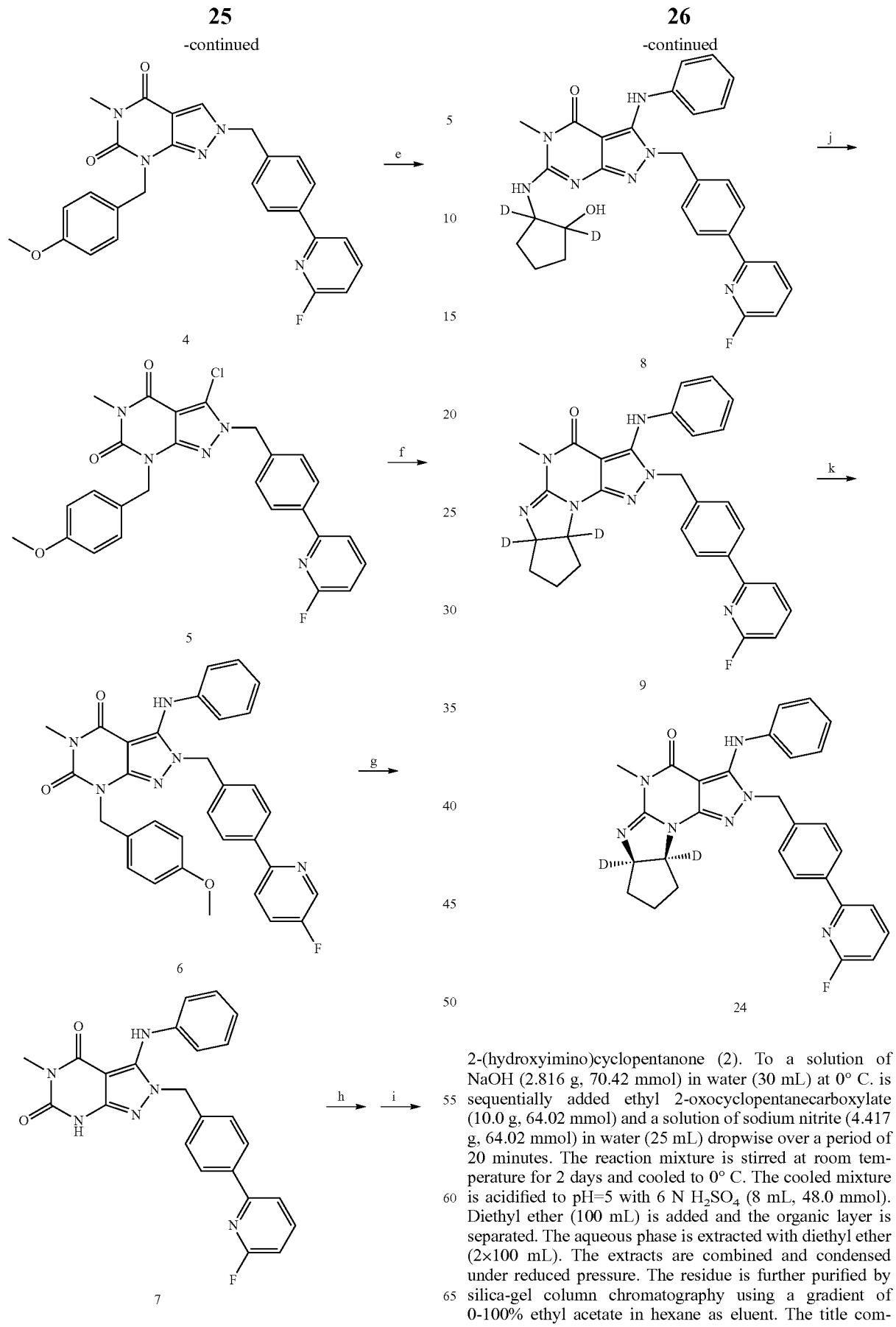

2-(hydroxyimino)cyclopentanone (2). To a solution of NaOH (2.816 g, 70.42 mmol) in water (30 mL) at 0° C. is sequentially added ethyl 2-oxocyclopentanecarboxylate (10.0 g, 64.02 mmol) and a solution of sodium nitrite (4.417 g, 64.02 mmol) in water (25 mL) dropwise over a period of 20 minutes. The reaction mixture is stirred at room temperature for 2 days and cooled to 0° C. The cooled mixture is acidified to pH=5 with 6 N $H_2SO_4$ (8 mL, 48.0 mmol). Diethyl ether (100 mL) is added and the organic layer is separated. The aqueous phase is extracted with diethyl ether (2×100 mL). The extracts are combined and condensed under reduced pressure. The residue is further purified by silica-gel column chromatography using a gradient of 0-100% ethyl acetate in hexane as eluent. The title compound 2 is given as a light brown solid (2.41 g, 33%).MS (ESI) m/z [M+H]$^+$. $^1$H NMR (500 MHz, Chloroform-d) δ 2.83 (t, J=7.5 Hz, 2H), 2.49 (t, J=7.9 Hz, 2H), 2.12-2.03 (m, 2H).

2-amino-1,2-dideuteriocyclopentanol (3). To a solution of 2-(hydroxyimino)cyclopentanone 2 (1.16 g, 10.26 mmol) in CH$_3$OD(7 mL) at 0° C. is added NaBD$_4$ (646 mg, 15.38 mmol) in small portions. The resulting mixture is stirred at 0° C. for 1 h and NiCl$_2$ is added, followed by NaBD$_4$ (646 mg, 15.38 mmol) in small portions. The mixture is stirred at 0° C. for 0.5 h and at room temperature for 2 h. The solvent is removed under reduced pressure and the residue is extracted with a mixture of CH$_2$Cl$_2$ and CH$_3$OH (10:1, 3×70 mL). The combined extracts are evaporated and further dried under high vacuum to give the title compound 3 as a light pink solid (0.88 g, crude). MS (ESI) m/z 104.04 [M+H]$^+$. This crude product is directly used for the next reaction without further purification.

3-chloro-2-(4-(6-fluoropyridin-2-yl)benzyl)-7-(4-methoxybenzyl)-5-methyl-2H-pyrazolo[3,4-d]pyrimidine-4,6(5H,7H)-dione (5) A solution of 2-(4-(6-fluoropyridin-2-yl)benzyl)-7-(4-methoxybenzyl)-5-methyl-2H-pyrazolo [3,4-d]pyrimidine-4,6(5H,7H)-dione 4 (9.04 g, 38.2 mmol) in THF (100 mL) is cooled to 0° C. under argon, and lithium bis(trimethylsilyl)amide in toluene (1M, 25.5 mL, 25.5 mmol) is added dropwise via a syringe. The reaction mixture is stirred at 0° C. for 4 h and quenched with water (30 mL). The mixture is stirred at room temperature for 5 min and the precipitate is filtered. The filtered cake is washed with water (100 mL) and then suspended in ethyl acetate (100 mL). The mixture is filtered, and the filtered cake is dried under high vacuum to give the title compound as a white solid (4.78 g, 45% yield). MS (ESI) ink 506.14 [M+H]$^+$.

2-(4-(6-fluoropyridin-2-yl)benzyl)-7-(4-methoxybenzyl)-5-methyl-3-(phenylamino)-2-pyrazolo[3,4-d]pyrimidine-4,6 (5H,7H)-dione (6). A suspension of 3-chloro-2-(4-(6-fluoropyridin-2-yl)benzyl)-7-(4-methoxybenzyl)-5-methyl-2H-pyrazolo [3,4-d]pyrimidine-4,6(5H,7H)-dione 5 (4.37 g, 8.65 mmol), aniline (1.18 mL, 13 mmol), cesium carbonate (5.63 g, 17.3 mmol), XPhos (1.6 g, 3.37 mmol), and tris(dibenzylideneacetone)dipalladium(O) (2.37 g, 2.6 mmol) in DMF (40 mL) is bubbled with argon at room temperature for 5 mins, and heated up to 100° C. The mixture is stirred at this temperature for 5 h until the reaction is completed. The solvent is evaporated and the residue is purified by silica-gel column chromatography with a gradient of 0-50% ethyl acetate in hexane. The title compound is given as an off-white solid (4.34 g, 89% yield). MS (ESI) ink 563.2019 [M+H]$^+$.

2-(4-(6-fluoropyridin-2-yl)benzyl)-5-methyl-3-(phenylamino)-2H-pyrazolo[3,4-d]pyrimidine-4,6(5H,7H)-dione (7). To a solution of 2-(4-(6-fluoropyridin-2-yl)benzyl)-7-(4-methoxybenzyl)-5-methyl-3-(phenylamino)-2H-pyrazolo [3,4-d]pyrimidine-4,6(5H,7H)-dione 6 (3.44 g, 6.11 mmol) in DCM (6 mL) at room temperature under argon is added trifluoroacetic acid (6.09 mL, 79.4 mmol), followed by trifluoromethanesulfonic acid (1.96 mL, 22 mmol). The resulting solution is stirred at room temperature for 2 h, and the solvents are removed under reduced pressure. The residue is neutralized with 7 N ammonium in methanol, and the mixture is evaporated to dryness. To the residue is added ethyl acetate (30 mL) and the resulting mixture is filtered. The filtered cake is washed with water (60 mL) and dried under high vacuum to generate the title compound 1.21 g. The filtrates are combined and evaporated to dryness. The residue is suspended in methanol (60 mL) and the suspension is filtered. The filtered cake is dried under vacuum to afford the title compound 0.94 g. (total 2.15 g, 79% yield). MS (ESI) m/z 443.1474 [M+H]$^+$. $^1$H NMR (500 MHz, DMSO-d$_6$) δ 11.52 (s, 1H), 8.77 (s, 1H), 8.12-8.03 (m, 1H), 7.99 (d, 2H), 7.90 (dd, J=7.6, 2.6 Hz, 1H), 7.25 (d, 2H), 7.18 (dd, J=8.5, 7.2 Hz, 2H), 7.13 (dd, J=8.1, 2.7 Hz, 1H), 6.91-6.75 (m, 3H), 5.27 (s, 2H), 3.34 (s, 2H), 3.08 (s, 3H), 2.63-2.41 (m, 2H).

6-((1,2-dideuterio-2-hydroxycyclopentyl)amino)-2-(4-(6-fluoropyridin-2-yl)benzyl)-5-methyl-3-(phenylamino)-2H-pyrazolo[3,4-d]pyrimidin-4(5H)-one (8). To a suspension of 2-(4-(6-fluoropyridin-2-yl)benzyl)-5-methyl-3-(phenylamino)-2H-pyrazolo[3,4-d]pyrimidine-4,6(5H,7H)-dione 7 (0.8 g, crude) and BOP (1.04 g, 2.35 mmol) in anhydrous THF (4 mL) at room temperature is added 8-diazabicyclo[5.4.0]undec-7-ene (0.83 mL, 5.45 mmol) under argon atmosphere. After the reaction mixture is stirred at room temperature for 5 minutes, solid 2-amino-1,2-dideuteriocyclopentanol (372 mg, crude) is added. The mixture is stirred at room temperature for 3 days. The solvent is removed, and the residue is purified by silica-gel column chromatography using a gradient of 0-100% a mixed solvent (CH$_2$Cl$_2$:CH$_3$OH:7 N NH$_3$ in methanol=10:1:0.1) in CH$_2$Cl$_2$ as eluent. The obtained product (1.80 g, brown solid) contains other impurities, which is directly used for the next reaction without further purification. MS (ESI) m/z 528.2061 [M+H]$^+$.

6a,9a-dideuterio-2-(4-(6-fluoropyridin-2-yl)benzyl)-5-methyl-3-(phenylamino)-5,6a,7,8,9,9a-hexahydrocyclopenta[4,5]imidazo[1,2-a]pyrazolo[4,3-e]pyrimidin-4(2H)-one (9). Thionyl chloride (0.360 mL, 4.96 mmol) is added dropwise to a stirred solution of 6-((1,2-dideuterio-2-hydroxycyclopentyl)amino)-2-(4-(6-fluoropyridin-2-yl)benzyl)-5-methyl-3-(phenylamino)-2H-pyrazolo[3,4-d]pyrimidin-4(5H)-one 8 (1.80 g, crude) in anhydrous DMF (10 mL) at room temperature under argon atmosphere. The reaction mixture is stirred for 2 h and the solvent is removed under reduced pressure. The residue is purified by silica-gel column chromatography with a gradient of 0-100% a mixed solvent (ethyl acetate:methanol:7 N ammonia in methanol=10:1:0.1) in ethyl acetate. The obtained product (332 mg) is further purified with a semipreparative HPLC system with a gradient of 0 to 30% acetonitrile in water containing 0.1% formic acid over 16 min. The title compound is given as an off-white solid (60 mg). MS (ESI) m/z 510.2071 [M+H]$^+$.

(6aS,9aR)-6a,9a-dideuterio-2-(4-(6-fluoropyridin-2-yl)benzyl)-5-methyl-3-(phenylamino)-5,6a,7,8,9,9a-hexahydrocyclopenta[4,5]imidazo[1,2-a]pyrazolo[4,3-e]pyrimidin-4(2H)-one. 6a,9a-dideuterio-2-(4-(6-fluoropyridin-2-yl)benzyl)-5-methyl-3-(phenylamino)-5,6a,7,8,9,9a-hexahydrocyclopenta[4,5]imidazo[1,2-a]pyrazolo[4,3-e]pyrimidin-4(2H)-one 9 (60 mg) is dissolved in a mixture of hexane, isopropanol and diethylamine (40:60:0.1 volume) (10 mL). The solution is loaded to a semipreparative HPLC system with a chiralpak AD-H column (20×250 mm) and eluted with a mixed solvent (of hexane, isopropanol and diethylamine (40:60:0.1 volume). The title compound is obtained as white solid (19 mg, 32% yield). MS (ESI) m/z 510.2743 [M+H]$^+$. 1H NMR (500 MHz, Chloroform-d) δ 7.92-7.86 (m, 2H), 7.86-7.80 (m, 1H), 7.58 (dd, J=7.6, 2.4 Hz, 1H), 7.31-7.26 (m, 2H), 7.13-7.07 (m, 1H), 7.07-7.02 (m, 2H), 6.97-6.90 (m, 2H), 6.89-6.81 (m, 2H), 4.94 (s, 2H), 3.34 (s, 3H), 1.96 (s, 1H), 1.86-1.79 (m, 1H), 1.77-1.70 (m, 2H), 1.63-1.52 (m, 2H).

Example 3

Synthesis of Novel [$^{14}$C] Radiolabeled PDE1 Inhibitor

A novel radiolabeled PDE1 inhibitor is synthesized according to the following Scheme:

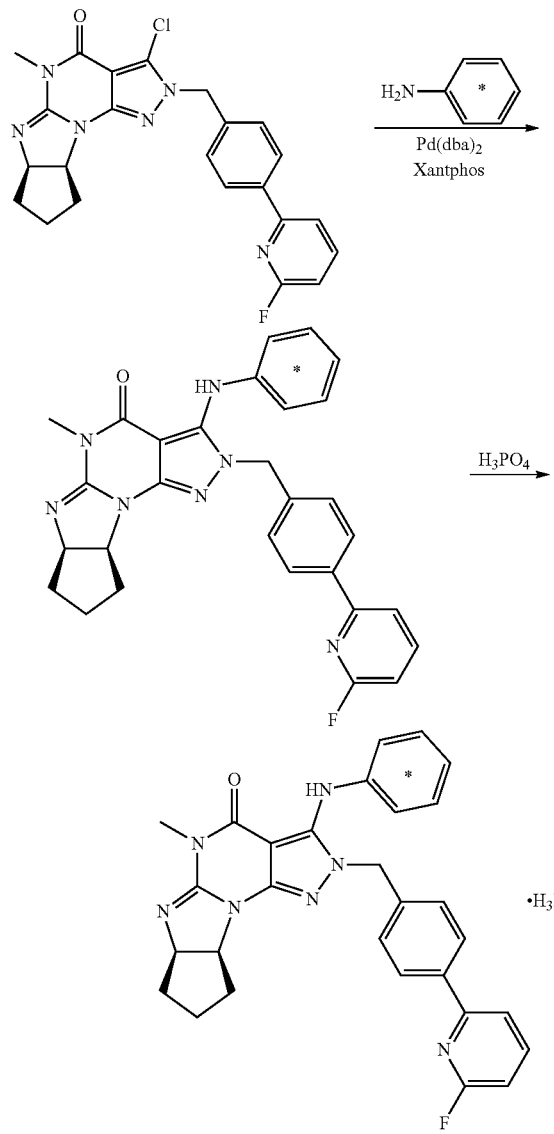

(6aR,9aS)-3-chloro-2-(4-(6-fluoropyridin-2-yl)benzyl)-5-methyl-5,6a,7,8,9,9a-hexahydrocyclopenta[4,5]imidazo[1,2-a]pyrazolo[4,3-e]pyrimidin-4(2H)-one is synthesized according to known methods, e.g., as disclosed in International Publications WO2009/075784A1 or WO2014/205354A1, both of which are incorporated herein by reference in their entireties. This compound is added to a mixture of [$^{14}$C] aniline, potassium carbonate, Xantphos and tris(dibenzylideneacetone)dipalladium(0), dissolved in 2-methyl-2-butanol (21 mL), frozen and pumped under high vacuum. The mixture was purged with nitrogen, heated, filtered and washed with ethanol.

The filtrate was purified firstly by column chromatography on silica eluting with ethyl acetate:ethanol followed by reverse phase high pressure liquid chromatography on a C18 column, eluting with aqueous trifluoroacetic acid:acetonitrile. The mixture was basified using potassium carbonate and was then partitioned between ethyl acetate and water. The solvent was removed with vacuum from the organic layer to give the [$^{14}$C] free base ((6aR,9aS)-2-(4-(6-fluoropyridin-2-yl)benzyl)-5-methyl-3-([U-14C]-phenylamino)-5,6a,7,8,9,9a-hexahydrocyclopenta[4,5] imidazo[1,2-a]pyrazolo[4,3-e]pyrimidin-4-(2H)-one).

The free base was dissolved in acetonitrile. The mixture was heated and a solution of phosphoric acid in acetonitrile was added under nitrogen. The mixture was then stirred under nitrogen. The mixture was filtered and washed with acetonitrile. The solid was dried over di-phosphorus pentoxide to give the phosphate salt ((6aR,9aS)-2-(4-(6-fluoropyridin-2-yl)benzyl)-5-methyl-3-([U-14C]-phenylamino)-5,6a,7,8,9,9a-hexahydrocyclopenta[4,5]imidazo[1,2-a]pyrazolo[4,3-e]pyrimidin-4-(2H)-one phosphate).

7. The compound according to claim 1, wherein the PDE1 inhibitor is a compound according to the following:
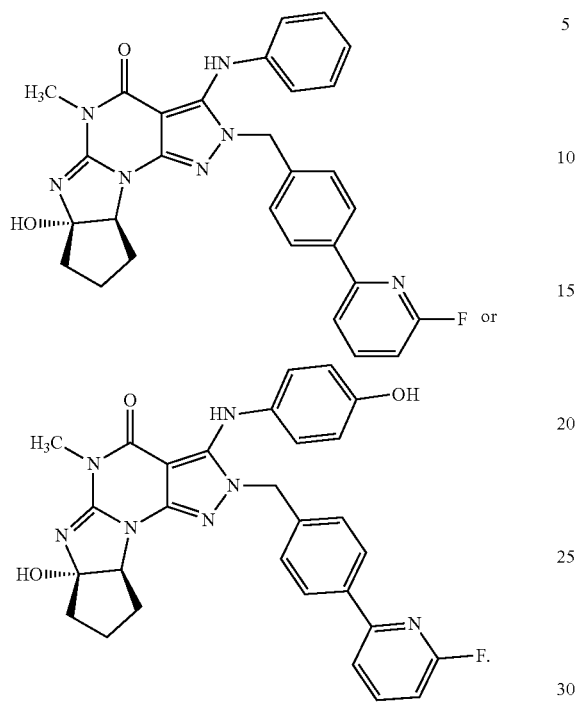

We claim:

1. A compound according to Formula Ia:

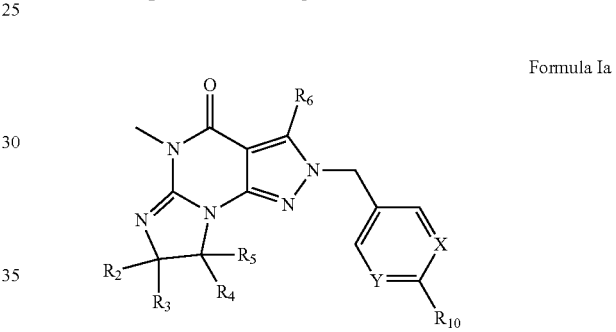

Formula Ia wherein
(i) $R_2$ and $R_5$ are independently H or hydroxy and $R_3$ and $R_4$ together form a tri- or tetra-methylene bridge;
(ii) $R_6$ is (optionally halo-substituted or hydroxy-substituted) phenylamino, (optionally halo-substituted or hydroxy-substituted) benzylamino, $C_{1-4}$alkyl, or $C_{1-4}$alkyl sulfide;
(iii) $R_{10}$ is $C_{1-4}$alkyl, methylcarbonyl, hydroxyethyl, carboxylic acid, sulfonamide, (optionally halo- or hydroxy-substituted) phenyl, (optionally halo- or hydroxy-substituted) pyridyl, or thiadiazolyl; and
X and Y are independently C or N,
wherein at least one of $R_2$ and $R_5$ are hydroxy,
optionally wherein at least one carbon atom is substituted with Carbon-14 ([$^{14}$C]),
in free or pharmaceutically acceptable salt form, or its enantiomers, diastereoisomers or racemates.

2. The compound according to claim 1, wherein $R_6$ is hydroxy-substituted phenylamino or hydroxy-substituted benzylamino.

3. The compound according to claim 1, wherein $R_6$ is hydroxy-substituted phenylamino.

4. The compound according to claim 1, wherein $R_2$ is hydroxy.

5. The compound according to claim 1, wherein $R_5$ is hydroxy.

6. The compound according to claim 1, wherein one carbon atom is substituted with Carbon-14 ([$^{14}$C]).